US012048548B2

(12) United States Patent
Kiuchi et al.

(10) Patent No.: US 12,048,548 B2
(45) Date of Patent: Jul. 30, 2024

(54) DISPLAY CONTROL DEVICE AND OPERATION METHOD OF DISPLAY CONTROL DEVICE

(71) Applicants: NIHON KOHDEN CORPORATION, Tokyo (JP); NATIONAL UNIVERSITY CORPORATION KOBE UNIVERSITY, Kobe (JP); NATIONAL UNIVERSITY CORPORATION SHIGA UNIVERSITY OF MEDICAL SCIENCE, Otsu (JP)

(72) Inventors: Kunihiko Kiuchi, Kobe (JP); Takashi Ashihara, Otsu (JP); Kaori Uchiyama, Tokorozawa (JP); Akio Ota, Tokorozawa (JP); Naoki Koura, Tokorozawa (JP); Koji Takizawa, Tokorozawa (JP)

(73) Assignees: NIHON KOHDEN CORPORATION, Tokyo (JP); NATIONAL UNIVERSITY CORPORATION KOBE UNIVERSITY, Hyogo (JP); NATIONAL UNIVERSITY CORPORATION SHIGA UNIVERSITY OF MEDICAL SCIENCE, Shiga (JP)

(*) Notice: Subject to any disclaimer, the term of this patent is extended or adjusted under 35 U.S.C. 154(b) by 132 days.

(21) Appl. No.: 17/691,385

(22) Filed: Mar. 10, 2022

(65) Prior Publication Data
US 2022/0296153 A1 Sep. 22, 2022

(30) Foreign Application Priority Data
Mar. 17, 2021 (JP) .................. 2021-043912

(51) Int. Cl.
*A61B 5/347* (2021.01)
*A61B 5/0245* (2006.01)
(Continued)

(52) U.S. Cl.
CPC ............ *A61B 5/339* (2021.01); *A61B 5/0245* (2013.01); *A61B 5/308* (2021.01); *A61B 5/347* (2021.01)

(58) Field of Classification Search
None
See application file for complete search history.

(56) References Cited

U.S. PATENT DOCUMENTS

2011/0251505 A1* 10/2011 Narayan .............. A61B 5/6852
600/515
2014/0088395 A1 3/2014 Dubois et al.
2019/0076041 A1 3/2019 Ashihara et al.

FOREIGN PATENT DOCUMENTS

WO 2011/127209 A1 10/2011

* cited by examiner

*Primary Examiner* — Ankit D Tejani
(74) *Attorney, Agent, or Firm* — Sughrue Mion, PLLC (57) ABSTRACT

A display control device includes processing circuitry configured to: obtain an intracardiac electrocardiogram of a subject; generate visualization data representing an excitation state of a myocardium based on the intracardiac electrocardiogram; determine a type of excitation dynamics of the myocardium based on the visualization data; and display, on a stereoscopic image of a heart of the subject, a site from which the intracardiac electrocardiogram is obtained with a color in accordance with a ratio of the determined type of the excitation dynamics.

7 Claims, 8 Drawing Sheets

(51) Int. Cl.
*A61B 5/308* (2021.01)
*A61B 5/339* (2021.01)

Multiple Wavelets

FIG. 2B

Passive Activation

FIG. 2A

Meandering Rotor

FIG. 8

DISPLAY CONTROL DEVICE AND OPERATION METHOD OF DISPLAY CONTROL DEVICE

CROSS-REFERENCE TO RELATED APPLICATIONS

This application is based on and claims priority under 35 USC 119 from Japanese Patent Application No. 2021-043912 filed on Mar. 17, 2021, the contents of which are incorporated herein by reference.

TECHNICAL FIELD

The presently disclosed subject matter relates to a display control device for displaying data obtained from a cardiac catheter and an operation method of a display control device.

BACKGROUND

In general, atrial fibrillation means arrhythmia in which convulsion of an atrium of a heart prevents proper action of the heart. When the atrial fibrillation occurs, since blood stagnates in an atrium and thrombus easily occurs, a risk of cerebral infarction or the like increases.

According to prior art, when arrhythmia such as atrial fibrillation occurs, a treatment is performed by selectively cauterizing (ablation) an abnormal site, which causes the arrhythmia, using a cardiac catheter. In order to perform this treatment, it is important to accurately identify a position to be ablated.

For example, specification of International Publication No. WO2011/127209A1 and US Patent Application Publication No. 2014/0088395 propose a technique for generating visualization data indicating an excitation state of a myocardium by performing an arithmetic processing on an intracardiac electrocardiogram measured from electrodes of a cardiac catheter, and identifying a position to be ablated from the visualization data.

The state of myocardial excitation during the atrial fibrillation is roughly classified into, for example, any one of several typical types referred to as excitation dynamics depending on a pattern of change in the state.

In the related art, a medical worker needs to determine a type of excitation dynamics of the myocardium by visually observing the state of the myocardium visualized based on the visualization data.

However, the state of the myocardium during the atrial fibrillation has a property of irregularly changing from moment to moment, and the change may be too fast to be visually recognized. Under such circumstances, in the related art, it is sometimes difficult for the medical worker to specify an abnormal site of the myocardium while visually determining the excitation dynamics.

Accordingly, an object of the presently disclosed subject matter is to provide a display control device and an operation method of a display control device, which are capable of supporting a medical worker to specify an abnormal site of a myocardium.

SUMMARY

A first aspect of the presently disclosed subject matter relates to a display control device including processing circuitry configured to: obtain an intracardiac electrocardiogram of a subject; generate visualization data representing an excitation state of a myocardium based on the intracardiac electrocardiogram; determine a type of excitation dynamics of the myocardium based on the visualization data; and display, on a stereoscopic image of a heart of the subject, a site from which the intracardiac electrocardiogram is obtained with a color in accordance with a ratio of the determined type of the excitation dynamics.

A second aspect of the presently disclosed subject matter relates to an operation method of a display control device including: obtaining, by an obtaining unit, an intracardiac electrocardiogram of a subject; generating, by a processor, visualization data representing an excitation state of a myocardium based on the intracardiac electrocardiogram; determining, by a determination unit, a type of excitation dynamics of the myocardium based on the visualization data; and displaying, by a display control unit, a site from which the intracardiac electrocardiogram is obtained with a color, on a stereoscopic image of the inside of an atrium of the subject, in accordance with a ratio of the determined type of the excitation dynamics.

BRIEF DESCRIPTION OF DRAWINGS

Exemplary embodiments of the presently disclosed subject matter will be described in detail based on the following figures, wherein.

DESCRIPTION OF EMBODIMENTS

Hereinafter, an example of the present embodiment will be described with reference to the drawings.

First Embodiment

Figure 1:
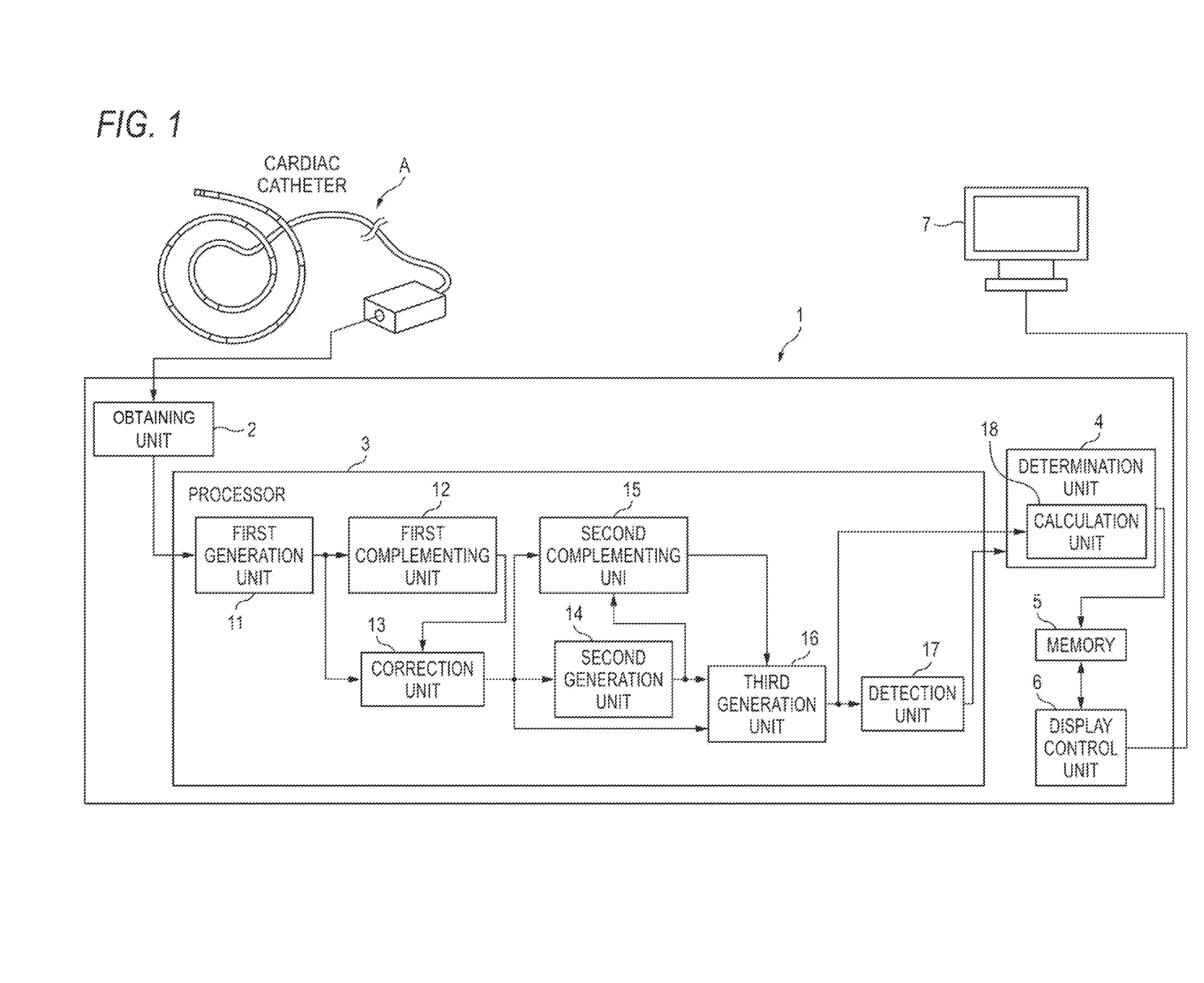
FIG. 1 is a schematic diagram of a display control device according to a first embodiment of the presently disclosed subject matter.

As illustrated in FIG. 1, a display control device 1 according to a first embodiment may include an obtaining unit 2, a processor 3, a determination unit 4, a memory 5, and a display control unit 6. The display control device 1 is used, for example, as a device for executing one or more functions in a catheter examination device. The display control device 1 is connected to a display device 7.

The obtaining unit 2 obtains an intracardiac electrocardiogram of a subject recorded by a recording unit (for example, a cardiac catheter A) having plural electrodes.

The processor 3 performs a processing for visualizing the excitation state of the myocardium of the subject on the intracardiac electrocardiogram obtained by the obtaining unit 2. The processor 3 may include a first generation unit 11, a first complementing unit 12, a correction unit 13, a second generation unit 14, a second complementing unit 15, a third generation unit 16, and a detection unit 17. The operation content of each unit of the processor 3 will be described later. The processor 2 is an example of processing circuitry.

The determination unit 4 determines the type of the excitation dynamics of the myocardium based on the visualization data. The determination unit 4 may include a calculation unit 18 for calculating a predetermined data number included in the visualization data. The visualization data for determining the type of the excitation dynamics of the myocardium is configured by frames for each predetermined time unit. The calculation unit 18 calculates the total number of predetermined grids included in the frame for each predetermined time unit as the predetermined data number included in the visualization data. The determination unit 4 determines the type of the excitation dynamics of the myocardium based on the predetermined number of grids calculated by the calculation unit 18 and the number of phase singularities detected by the detection unit 17.

Figure 2A:
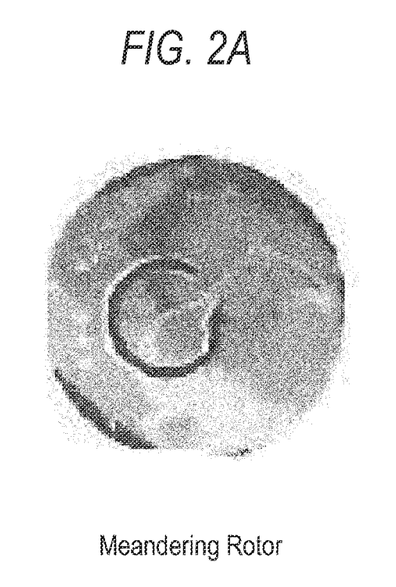
FIG. 2A is a diagram illustrating excitation dynamics of a typical type of a myocardium.
Figure 2B:
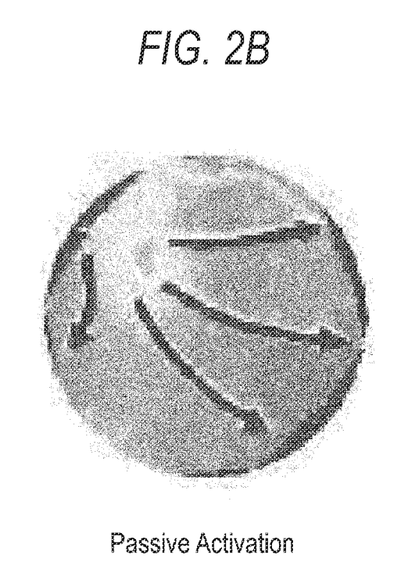
FIG. 2B is a diagram illustrating excitation dynamics of a typical type of a myocardium.
Figure 2C:
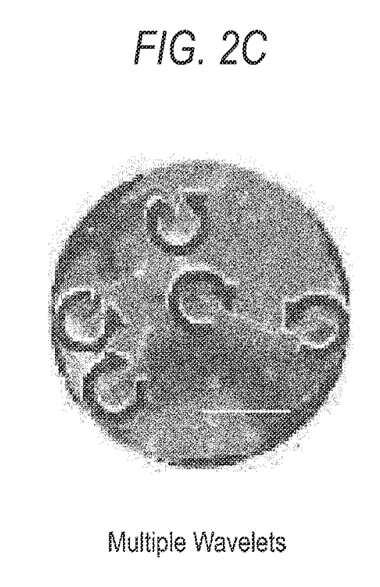
FIG. 2C is a diagram illustrating excitation dynamics of a typical type of a myocardium.

The type of the excitation dynamics of the myocardium means a pattern of a change in the state of the myocardium in which atrial fibrillation occurs. Types of the excitation dynamics of the myocardium are roughly classified into, for example, a meandering rotor (MR) as illustrated in FIG. 2A, a passive activation (PA) as illustrated in FIG. 2B, and multiplex wavelets (MW) as illustrated in FIG. 2C. The PA means a state (an example of a first state) in which an excitation wave propagates. The MR means a state (an example of a second state) in which an excitation wave is rotating around a phase singularity. The MW means a state (an example of a third state) in which plural phase singularities exist at the same time.

Figure 7:
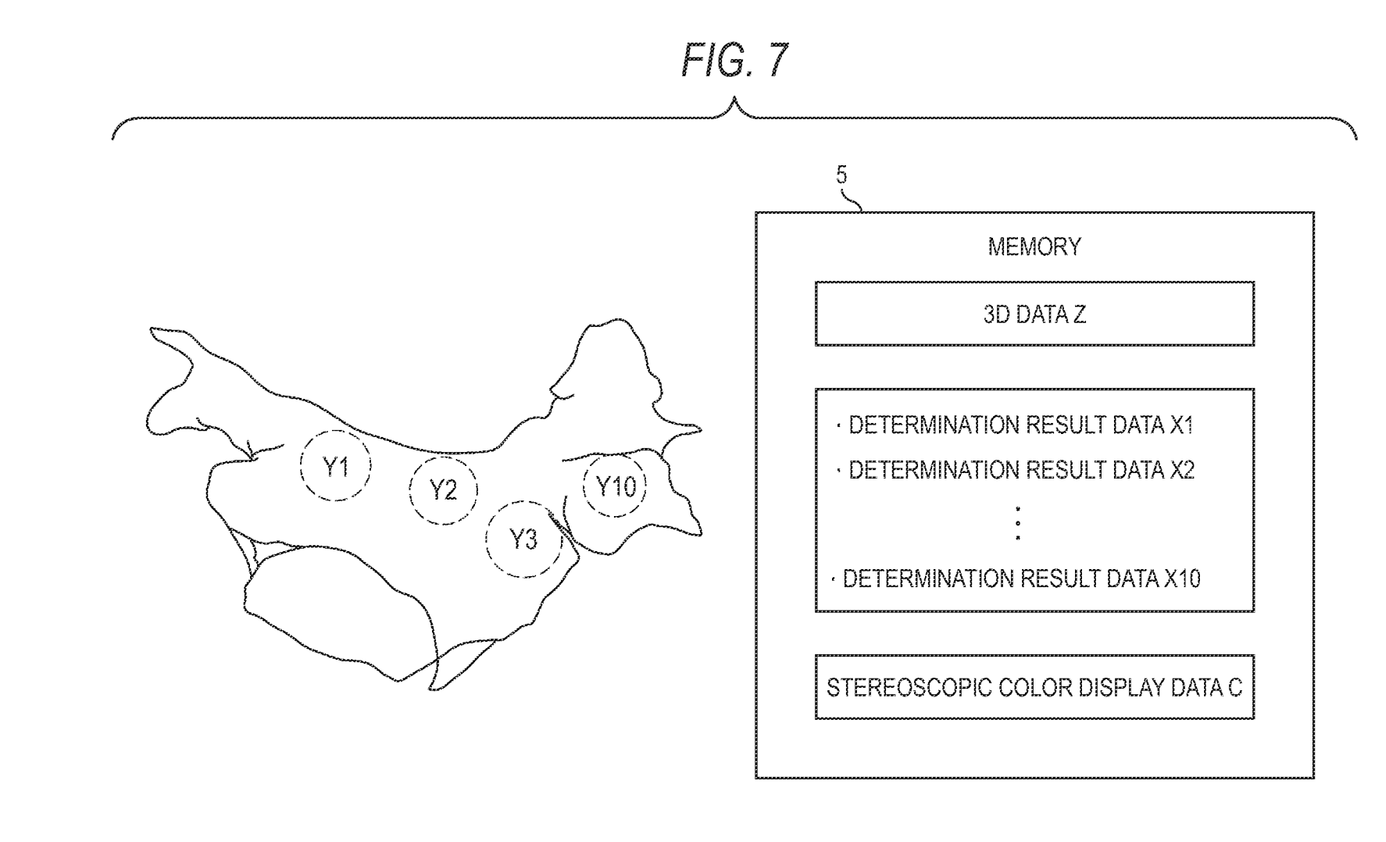
FIG. 7 is a diagram for explaining a data configuration of a memory.

The memory 5 stores 3D data Z forming a stereoscopic image of the heart of the subject, determination result data X1 to X10 by the determination unit 4, and stereoscopic color display data C (see FIG. 7).

The display control unit 6 obtains data from the memory 5, generates the stereoscopic color display data C, and transmits the stereoscopic color display data C to the display device 7. The display device 7 may include, for example, a liquid crystal monitor screen on a touch panel.

Next, an operation of the display control device 1 will be described with reference to FIGS. 3 to 8.

Figure 3:
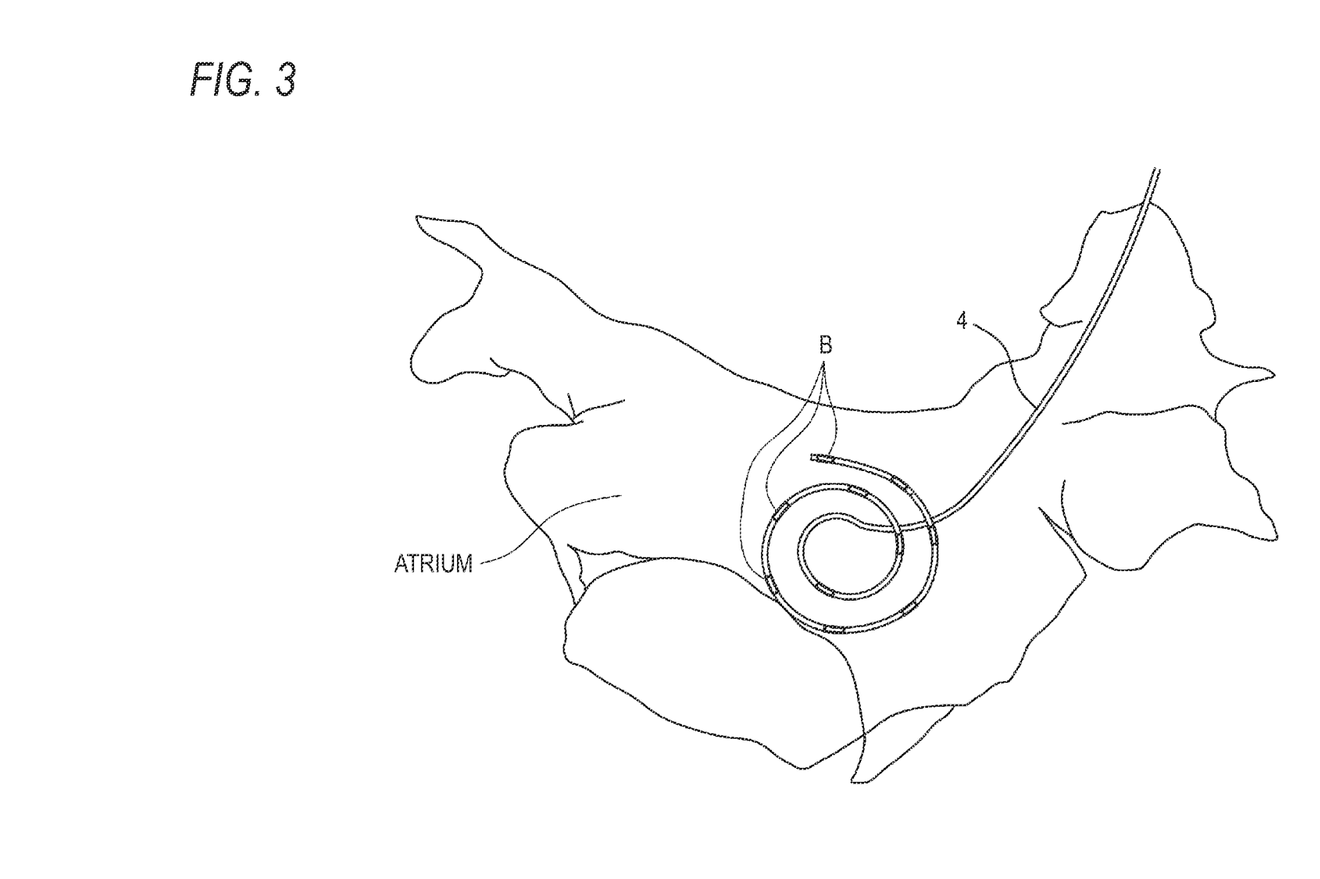
FIG. 3 is a schematic diagram illustrating a catheter placed in an atrium.
Figure 4:
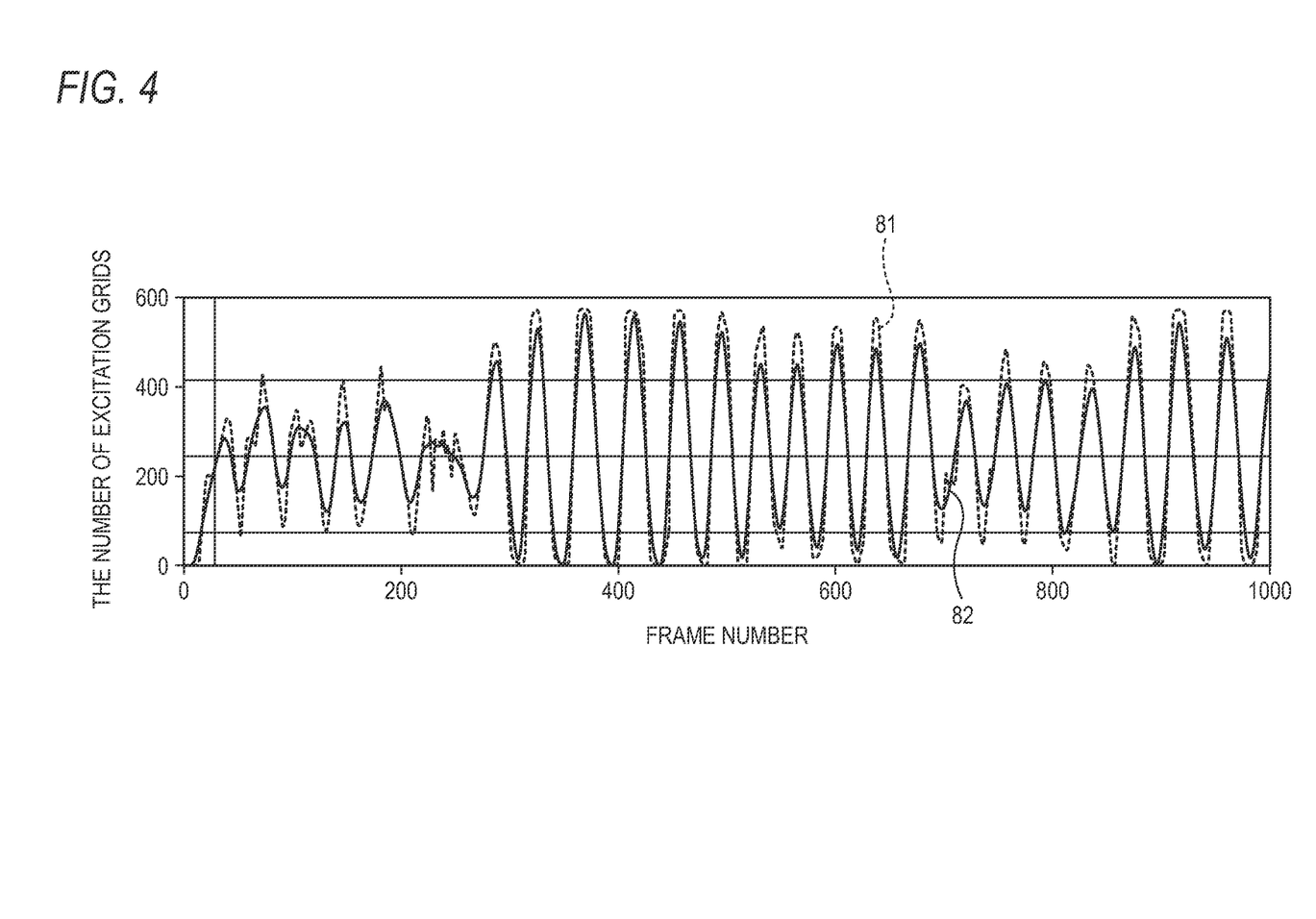
FIG. 4 is a diagram for explaining the number of excitation grids included in frames constituting visualization data.

As illustrated in FIG. 3, first, the cardiac catheter A having plural electrodes B is inserted into the atrium of the subject and placed at a predetermined position for a predetermined time (for example, 10 seconds in one attempt).

Plural intracardiac electrocardiogram waveforms (ten intracardiac electrocardiogram waveforms in this example) are recorded by the electrodes B of the cardiac catheter A. The recorded intracardiac electrocardiogram waveform is obtained by the obtaining unit 2.

Next, the first generation unit 11 generates a pseudo action potential waveform for each of the plural intracardiac electrocardiograms obtained by the obtaining unit 2. The first complementing unit 12 defines a virtual electrode at a position where the electrode of the inserted cardiac catheter A is not arranged, that is, a position where a distance from a surrounding electrode is large among plural electrodes arranged, in the myocardium in the atrium. The first complementing unit 12 complements the pseudo action potential waveform for the virtual electrode based on the pseudo action potential waveform generated for the electrodes around the virtual electrode.

The correction unit 13 removes noise components included in the pseudo action potential waveform output from the first generation unit 11 and the first complementing unit 12, and performs correction to make amplitudes of the respective beats uniform.

The second generation unit 14 generates a shift waveform in which a time phase is shifted by a predetermined time with respect to an action potential waveform, with respect to the action potential waveform output from the correction unit 13.

The second complementing unit 15 complements an action potential waveform and a shift waveform based on the action potential waveform and the shift waveform generated for the surrounding electrodes with respect to a position where the electrode and the virtual electrode of the cardiac catheter A are not arranged, that is, a position where the distance between each electrode and the surrounding electrodes is large.

The third generation unit 16 generates a phase portrait based on the action potential waveform output from the correction unit 13, the shift waveform output from the second generation unit 14, and the action potential waveform and the shift waveform output from the second complementing unit 15. In addition, the third generation unit 16 calculates a phase based on the phase portrait, and generates visualization data (phase map) representing an excitation state of the myocardium. The visualization data means frames in which an excitation potential of the myocardium is visualized. Electrical excitation occurs in a membrane potential of myocardial cells, which acts to contract the heart. The excitation contraction phenomenon is caused by an action potential. The action potential means an excitation reaction of the myocardial cells by depolarization caused by inflow of Na$^+$ into cells and repolarization caused by inflow or outflow of Ca$2^+$ or K$^+$.

The detection unit 17 detects a phase singularity in the visualization data generated by the third generation unit 16, that is, a cause site (rotor) of fibrillation on an atrial wall.

The determination unit 4 causes the calculation unit 18 to sequentially calculate the number of excitation grids included in each frame in the visualization data generated by the third generation unit 16. The excitation grid means a grid indicating the excitation state of the myocardium, and is, for example, a grid drawn in a warm color indicating R=255. The number of excitation grids of each frame calculated by the calculation unit 18 is illustrated as a graph 81 in FIG. 4, for example. Further, the determination unit 4 causes the calculation unit 18 to sequentially calculate moving averages of the number of excitation grids included in the frames (for example, 15 frames) within a predetermined time. The moving average number of excitation grids is illustrated by, for example, a graph 82 in FIGS. 4 and 5.

The determination unit 4 calculates, for example, an average value of the number of excitation grids, and sets positive and negative threshold values based on the calculated average number of excitation grids. The average number of excitation grids is illustrated as, for example, an average value 83 in FIG. 5, and the positive and negative threshold values are respectively illustrated as, for example, threshold values 84a, 84b in FIG. 5. The determination unit 4 determines whether the moving average number of excitation grids exceeds the threshold values 84a, 84b, and determines that the excitation dynamics of the myocardium is PA when the moving average number of excitation grids exceeds the threshold values 84a, 84b. In the graph 82 illustrated in FIG. 5, the moving average number of excitation grids exceeds the threshold values 84a, 84b in a range

Figure 5:
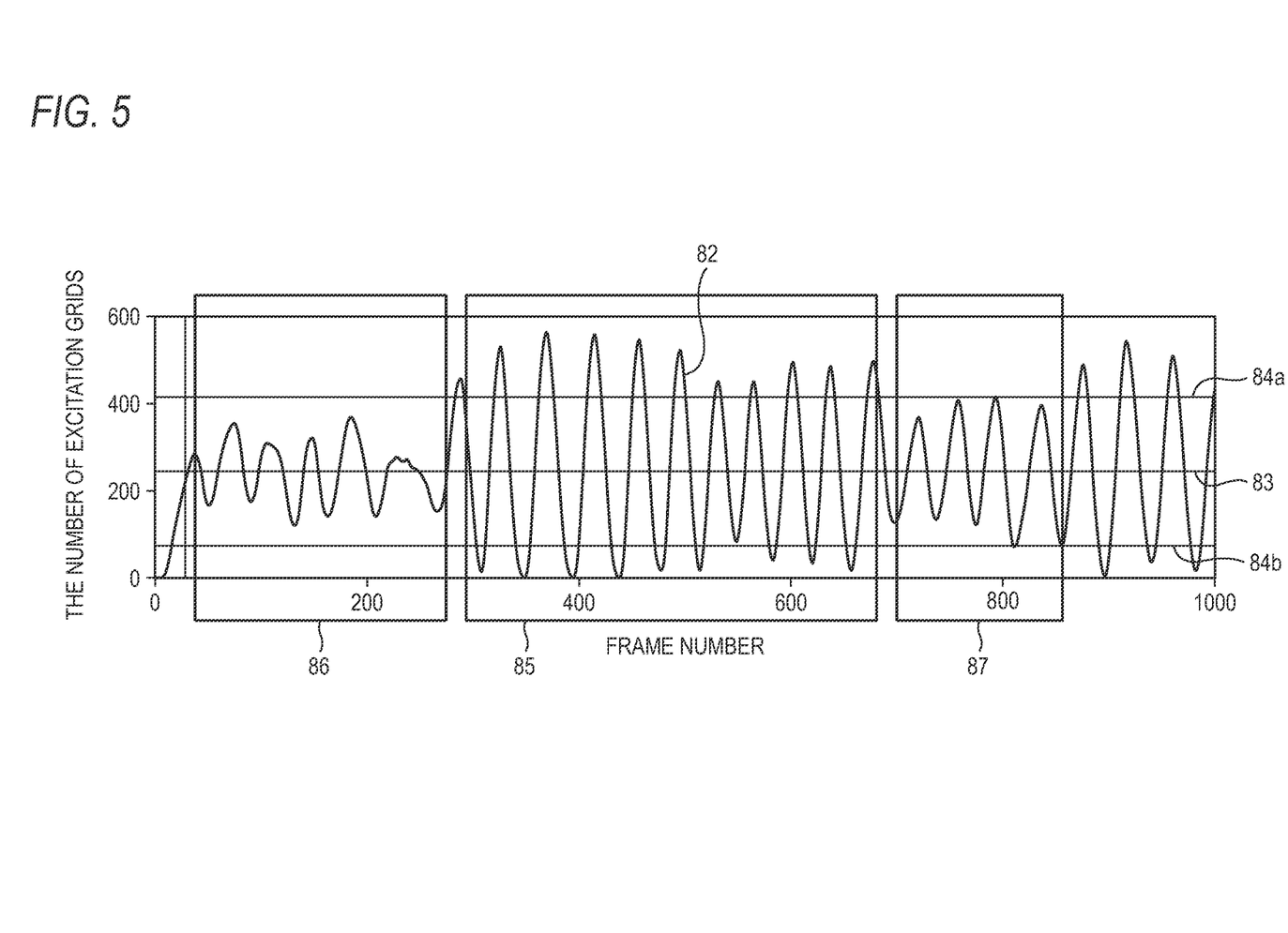
FIG. 5 is a diagram for explaining a method of determining the type of the excitation dynamics of the myocardium.

85, for example, and the excitation dynamics of the myocardium in this time zone is determined as PA. When the moving average number of excitation grids exceeds the threshold value, a position of the excitation grid in each frame may be specified to determine whether the excitation wave is generated in the region of the cardiac catheter A or is generated outside the region. In this way, the excitation state PA of the myocardium is further divided into two.

When the moving average number of excitation grids does not exceed the threshold values 84a, 84b (for example, ranges 86, 87 in FIG. 5), the determination unit 4 determines the type of the excitation dynamics of the myocardium based on the number of phase singularities 62 of the frame detected by the detection unit 17. The determination unit 4 determines that the excitation dynamics of the myocardium is MW when there are plural phase singularities of the frame, and determines that the excitation dynamics of the myocardium is MR when there are not plural phase singularities.

Figure 6:
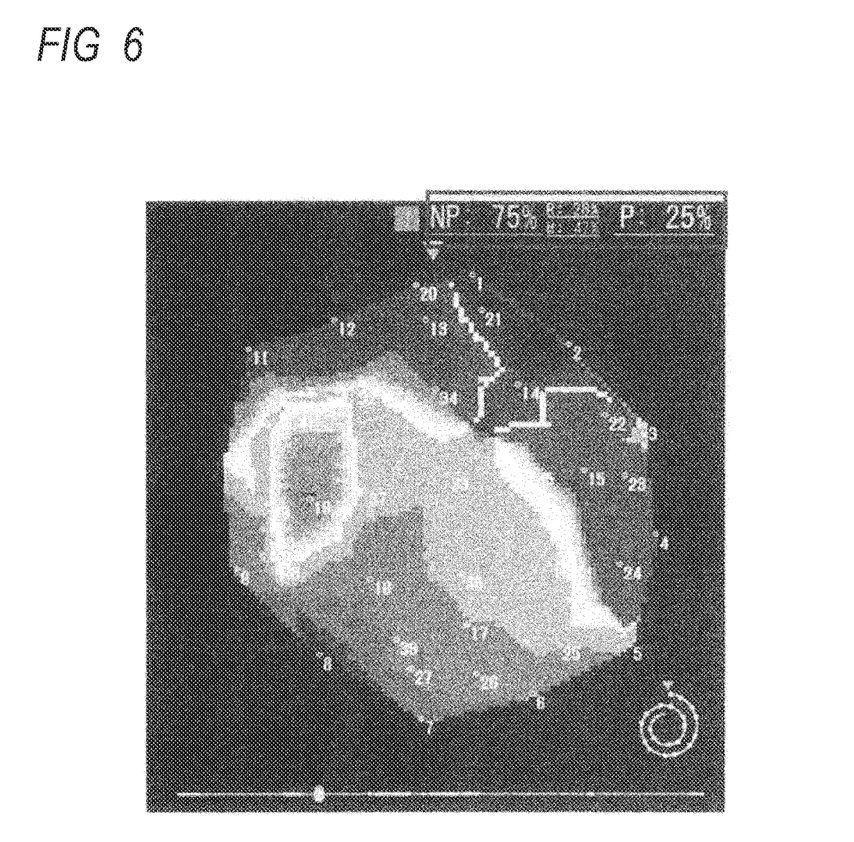
FIG. 6 is an image diagram in a case where the visualization data is continuously displayed in time series.

FIG. 6 illustrates an image of a movie in a case where the visualization data is continuously displayed in time series, and depicts a state in which the excitation state of the myocardium of the subject changes in real time. The move is played for a time period (for example, 5 seconds) during which the intracardiac electrocardiogram is obtained in one attempt using the cardiac catheter A. The movie may be played at a double speed (or another speed, for example, 1/10 times speed). As illustrated in FIG. 6, at the same time as start of the movie, determination results (types and ratios of the excitation dynamics) in an entire area of the movie are displayed. Specifically, the meandering rotor (R)=28%, the multiple wavelets (M)=47%, the sum of (R) and (M) (non passive ratio: NP)=75%, and the passive activation (P)=25% are displayed. The determination result data is stored in the memory 5 as the determination result data X1 at a predetermined position Y1 in the atrium.

Thereafter, as illustrated in FIG. 7, the cardiac catheter A is sequentially moved to predetermined positions Y2 to Y10 in the atrium, and the determination result data X2 to X10 are stored in the memory 5 by the same processing. In the present example, for convenience of description, the process from the obtaining of the intracardiac electrocardiogram to the process of obtaining the determination result data has been described as a series of processes, but the presently disclosed subject matter is not limited thereto. For example, first, the cardiac catheter A may be sequentially moved to the predetermined positions Y1 to Y10 in the atrium, data of the intracardiac electrocardiogram waveforms at the respective positions may be prepared and stored, and then the determination result data may be obtained for the respective data.

After the determination result data X1 to X10 at the predetermined positions Y1 to Y10 in the atrium are stored in the memory 5, the display control unit 6 generates the stereoscopic color display data C based on the 3D data Z forming the stereoscopic image of the heart and the determination result data X1 to X10, and stores the stereoscopic color display data C in the memory 5.

At this time, the display control unit 6 determines colors to be displayed at respective positions on the stereoscopic image corresponding to the predetermined positions Y1 to Y10 based on predetermined excitation dynamics, for example, the ratio of "non passive ratio: NP", and a predetermined color standard with respect to the respective determination result data X1 to X10.

Figure 8:
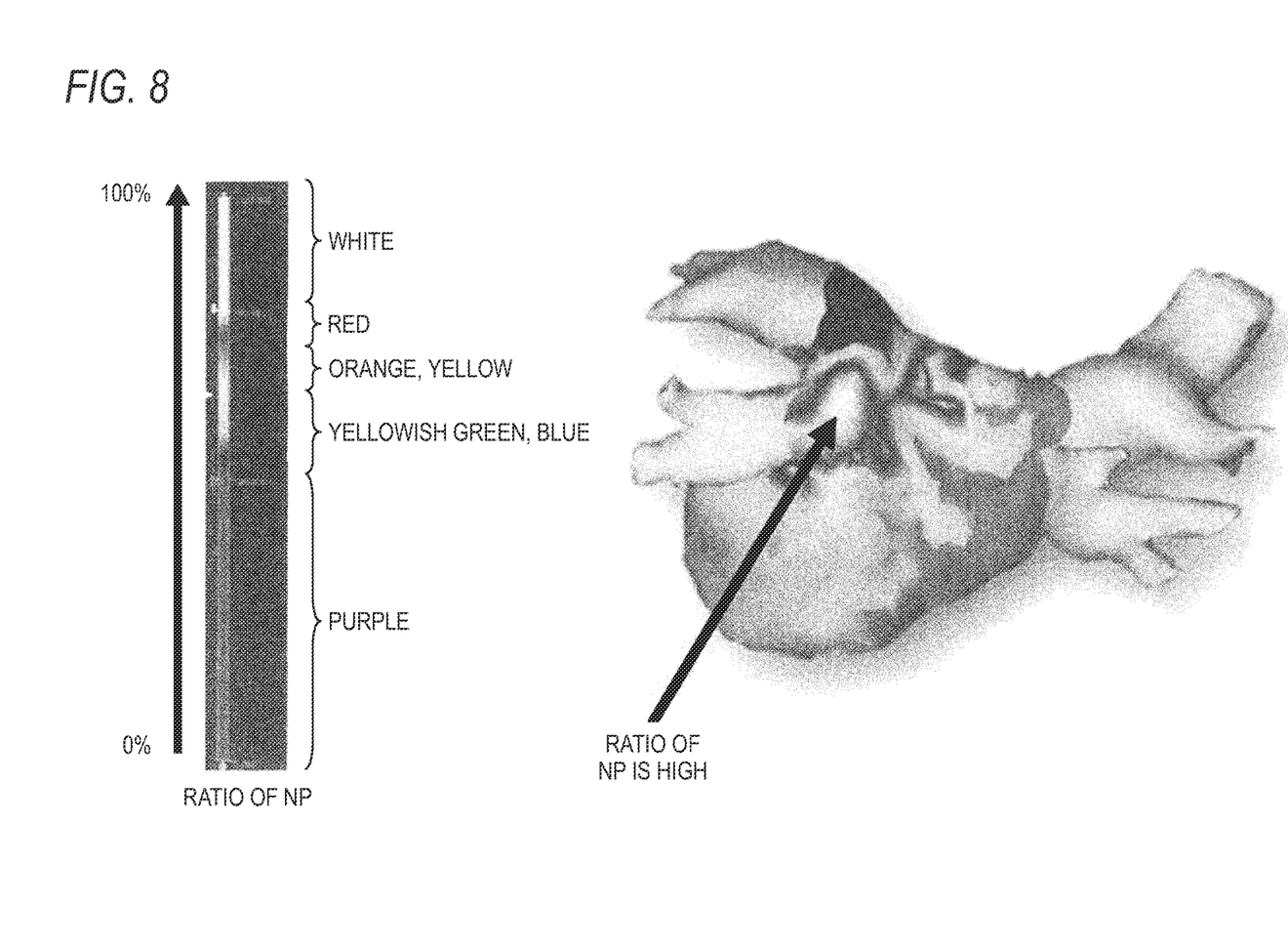
FIG. 8 is an image diagram when a 3D image of the heart of a patient is displayed.

As shown in FIG. 8, the color standard is, for example, a standard in which "non passive ratio: NP" changes stepwise from 0% to 100% in an order of white, red, orange, yellow, yellowish green, blue, and purple. The display control unit 6 sequentially complements a region between the predetermined portion Y1 and the predetermined portion Y2 with colors so that the colors change stepwise along the color standard from the color (for example, white) of the predetermined portion Y1 to the color (for example, purple) of the predetermined portion Y2. In this manner, the display control unit 6 completes the stereoscopic color display data C related to the entire heart of the patient, transmits the stereoscopic color display data C to the display device 7, and causes the stereoscopic color display data C to be displayed on the screen thereof.

FIG. 8 is an image diagram when a 3D image of the heart of the patient is displayed on the display device 7 based on the stereoscopic color display data C. Specifically, FIG. 8 is an example when the ratio of "non passive ratio: NP" is displayed with a color (color mapping) on the 3D image of the atrium.

In the related art, when the medical worker determines the type of the excitation dynamics of the myocardium, the visualization data indicating the excitation state of the myocardium is generated, and the type of excitation dynamics is visually determined based on the visualization data. However, the myocardium during the atrial fibrillation may generate vibration about 300 times per minute, for example, and it is difficult to visually and accurately determine the excitation dynamics from data of the myocardium that changes at such a high speed.

In contrast, according to the display control device 1 of the present embodiment, the stereoscopic color display data C is generated based on the determination result data X1 to X10 and the color standard. When the display control unit 6 transmits the stereoscopic color display data C to the display device 7 and causes the stereoscopic color display data C to be displayed, the ratio of "non passive ratio: NP" is displayed with a color on the 3D image of the heart as illustrated in FIG. 8. For this reason, the medical worker can visually and intuitively grasp a region in which the ratio of NP is high, and it is easy to make a treatment strategy.

The presently disclosed subject matter is not limited to the above embodiment and may be modified or improved as appropriate. In addition, materials, shapes, dimensions, numerical values, forms, numbers, arrangement places, and the like of the respective constituent elements in the above-described embodiment are optional and are not limited as long as the presently disclosed subject matter can be achieved.

For example, in the above embodiment, the phase portrait and the visualization data are generated using the action potential waveform and the shift waveform, and the type of the excitation dynamics of the myocardium is determined based on the visualization data. However, the presently disclosed subject matter is not limited to this configuration, and for example, a phase portrait and visualization data may be generated by performing Hilbert transform on an intracardiac electrocardiogram, and the type of the excitation dynamics of the myocardium may be determined based on the visualization data.

Further details of an exemplary method for determining myocardial excitation are described in "MYOCARDIAL EXCITATION DETERMINING APPARATUS" of U.S. Patent Application Publication No. 2019/0076041 filed on Mar. 14, 2017, and the entire disclosure thereof is incorporated herein by reference. All of the features described in the presently disclosed subject matter can be implemented together with the features described in the present specification.

The aforementioned embodiments are summarized as follows.

A first aspect of the presently disclosed subject matter relates to a display control device including processing circuitry configured to: obtain an intracardiac electrocardiogram of a subject; generate visualization data representing an excitation state of a myocardium based on the intracardiac electrocardiogram; determine a type of excitation dynamics of the myocardium based on the visualization data; and display, on a stereoscopic image of a heart of the subject, a site from which the intracardiac electrocardiogram is obtained with a color in accordance with a ratio of the determined type of the excitation dynamics.

According to this configuration, a ratio of the type of the determined excitation dynamics (for example, a ratio of "non passive ratio: NP") is displayed with a color on a stereoscopic image of the heart, so that the medical worker can visually and intuitively grasp a region which is highly likely to be an abnormal site of the myocardium, and the medical worker can easily make a treatment strategy.

A second aspect of the presently disclosed subject matter relates to an operation method of a display control device including: obtaining, by an obtaining unit, an intracardiac electrocardiogram of a subject; generating, by a processor, visualization data representing an excitation state of a myocardium based on the intracardiac electrocardiogram; determining, by a determination unit, a type of excitation dynamics of the myocardium based on the visualization data; and displaying, by a display control unit, a site from which the intracardiac electrocardiogram is obtained with a color, on a stereoscopic image of the inside of an atrium of the subject, in accordance with a ratio of the determined type of the excitation dynamics.

According to the above aspect, it is possible to provide the display control device and the operation method of a display control device that are capable of supporting the medical worker to specify the abnormal site of the myocardium.

The invention claimed is:

1. A display control device comprising processing circuitry configured to:
    obtain an intracardiac electrocardiogram of a subject for a predetermined time period;
    generate visualization data representing excitation states of a myocardium based on the intracardiac electrocardiogram during the predetermined time period;
    determine types of excitation dynamics of the myocardium during the predetermined time period based on the visualization data; and
    display, on a stereoscopic image of a heart of the subject, a site from which the intracardiac electrocardiogram is obtained with a color in accordance with a ratio of time of the determined types of the excitation dynamics of the myocardium during the predetermined time period.

2. The display control device according to claim 1,
    wherein the type of the excitation dynamics of the myocardium includes a first state (PA) indicating a state in which an excitation wave propagates, a second state (MR) indicating a state in which an excitation wave is rotating around a phase singularity representing a center of turning of the excitation state of the myocardium, and a third state (MW) indicating a state in which a plurality of the phase singularities exist, and
    wherein the processing circuitry is configured to display, on the stereoscopic image of the heart of the subject, a site from which the intracardiac electrocardiogram is obtained with a color in accordance with a total ratio of the second state and the third state.

3. The display control device according to claim 1,
    wherein the visualization data is configured by frames for each predetermined time unit, and each of the frames is configured by a plurality of grids, and
    wherein the processing circuitry is configured to calculate a total number of excitation grids indicating the excitation state of the myocardium among the plurality of grids constituting the frame, and determine the type of the excitation dynamics of the myocardium based on the total number of the excitation grids for each frame and the total number of the phase singularities.

4. The display control device according to claim 1,
    wherein the processing circuitry is configured to obtain, a plurality of times sequentially, an intracardiac electrocardiogram over an entire inside of an atrium of the subject,
    wherein the processing circuitry is configured to generate the visualization data for each of the obtained intracardiac electrocardiograms,
    wherein the processing circuitry is configured to determine the type of the excitation dynamics for each site from which the intracardiac electrocardiogram is obtained, and
    wherein the processing circuitry is configured to perform color display on the stereoscopic image of the heart of the subject in accordance with the ratio of the determined type of the excitation dynamics for each site from which the intracardiac electrocardiogram is obtained.

5. An operation method of a display control device, comprising:
    obtaining, by an obtaining unit, an intracardiac electrocardiogram of a subject for a predetermined time period;
    generating, by a processor, visualization data representing excitation states of a myocardium based on the intracardiac electrocardiogram during the predetermined time period;
    determining, by a determination unit, types of excitation dynamics of the myocardium during the predetermined time period based on the visualization data; and
    displaying, by a display control unit, on a stereoscopic image of the inside of an atrium of the subject, a site from which the intracardiac electrocardiogram is obtained with color in accordance with a ratio of a time of the determined types of the excitation dynamics of the myocardium during the predetermined time period.

6. The operation method according to claim 5, wherein:
    the ratio of the determined type of the excitation dynamics is a total ratio of a second state (MR) indicating a state in which an excitation wave is rotating around a phase singularity representing a center of turning of the excitation state of the myocardium and a third state (MW) indicating a state in which a plurality of the phase singularities exist.

7. The operation method according to claim 5, wherein:
the visualization data is configured by frames for each predetermined time unit, and each of the frames is configured by a plurality of grids; and
the determining of the type of excitation dynamics of the myocardium includes calculating a total number of excitation grids indicating the excitation state of the myocardium among the plurality of grids constituting the frame, and determining the type of the excitation dynamics of the myocardium based on the total number of the excitation grids for each frame and the total number of the phase singularities.

\* \* \* \* \*